United States Patent [19]  [11] 4,317,459
Gilman  [45] Mar. 2, 1982

[54] FIXATION LOOP FOR TRANSVENOUS LEADS

[75] Inventor: Byron L. Gilman, Maple Grove, Minn.

[73] Assignee: Medtronic, Inc., Minneapolis, Minn.

[21] Appl. No.: 190,691

[22] Filed: Sep. 25, 1980

Related U.S. Application Data

[63] Continuation of Ser. No. 53,003, Jun. 28, 1979, abandoned.

[51] Int. Cl.³ .............................................. A61N 1/04
[52] U.S. Cl. ................................. 128/785; 128/419 P
[58] Field of Search ................... 128/419 P, 784, 785, 128/DIG. 26

[56] References Cited

U.S. PATENT DOCUMENTS 3,726,280 4/1973 Lacount ..................... 128/DIG. 26
4,136,701 1/1979 Barton et al. .................... 128/419 P
4,154,247 5/1979 O'Neill ............................ 128/419 P Primary Examiner—William E. Kamm
Attorney, Agent, or Firm—John L. Rooney; Joseph F. Breimayer; Carl A. Forest

[57] ABSTRACT

Transvenous leads including an outer atrial and an inner ventricular spaced wound coils coaxial with respect to each other and including a closed fixation loop connected to the outer lead. The closed fixation loop extends outwardly at an angle with respect to the outer lead. An inner lead is slideably adjustable within the outer lead and supports a ventricular electrode. The outer lead supports an atrial electrode. A connector at the other end of the leads supports and secures a connector pin for the outer lead in one sleeve and provides for slideable adjustment of the inner lead which includes a proximal tip in the other sleeve. An O-ring engages in an O-ring groove in the other sleeve to provide a liquid seal between the atrial coil and the end of the ventricular coil. The proximal tip and connector pin connect to a pulse generator. The transvenous leads with the closed fixation loop are intended for pacing the ventricular and atrial chambers of a heart.

13 Claims, 5 Drawing Figures

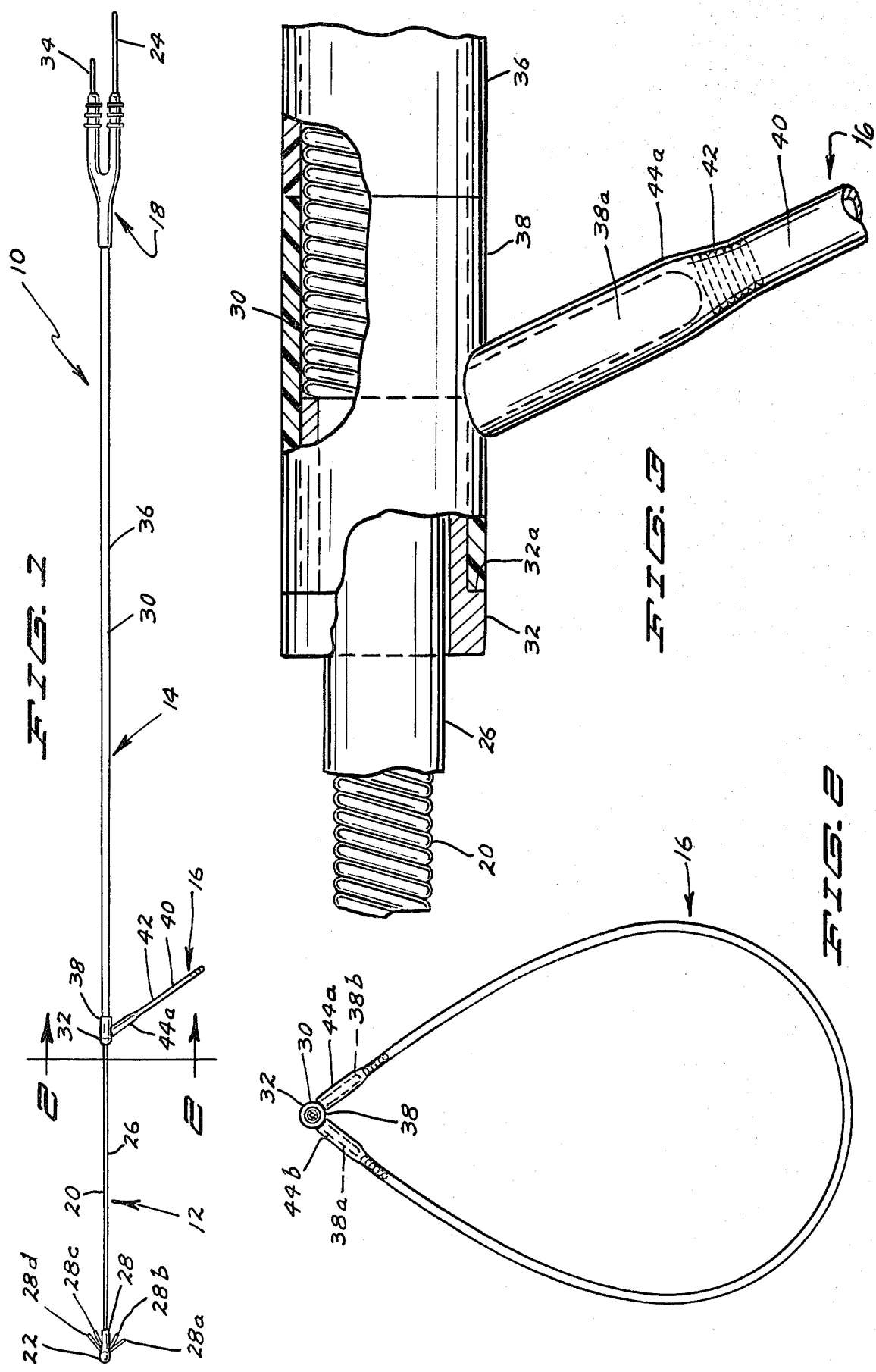

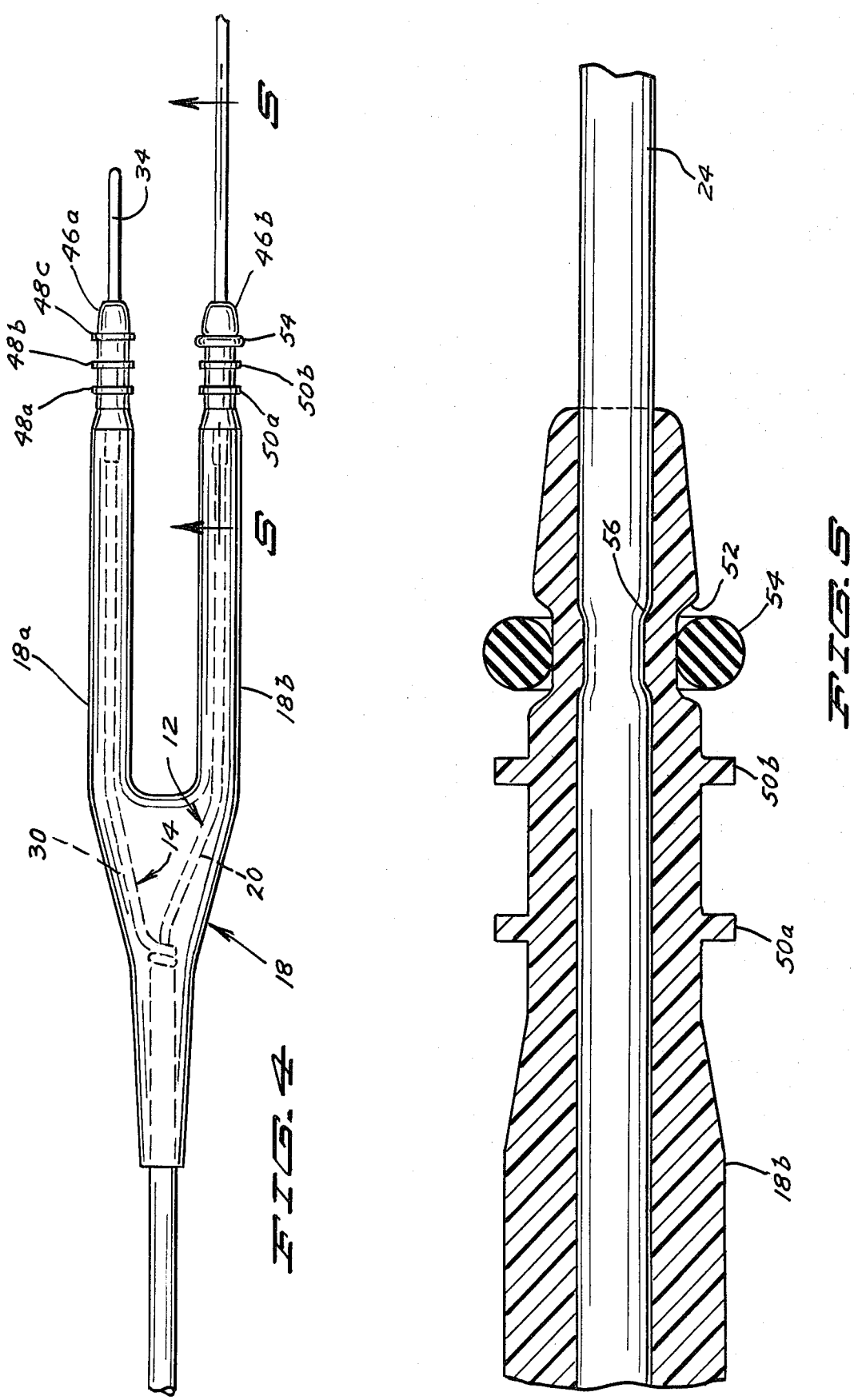

FIXATION LOOP FOR TRANSVENOUS LEADS

CROSS REFERENCE TO CO-PENDING APPLICATION

This is a continuation of application Ser. No. 053,003 filed June 28, 1979 now abandoned.

BACKGROUND OF THE INVENTION

1. Field of the Invention

The present invention relates generally to a surgical electrical applicator, and more importantly, pertains to a closed fixation loop for transvenous leads.

2. Description of the Prior Art

There has never been a coaxial sliding pacing lead for connecting between a chamber or chambers of a heart and a pulse generator. In the past, it always has been a prior art practice to either securely affix an electrode or electrodes to walls of the heart or in the alternative, to let the electrode of a pacing lead lie adjacent to the wall.

In pacing the atrial chamber, it has been a prior art practice to let the electrode of the atrial lead lie adjacent to the atrial wall. The lead was never affixed to the atrial wall because of the thinness of the wall and subsequent damage to the wall until recent developments in pinch-on electrodes. Prior art atrial leads have been previously anchored by a hook or J-shape with tines on the end but a J-shape requires diverging distal ends which are not compatible with a sliding coaxial lead. Atrial ventricle coaxial leads usually do not have diverging ends.

The present invention overcomes the disadvantages of the prior art problems in providing a closed fixation loop for an A-V transvenous lead.

SUMMARY OF THE INVENTION

The present invention provides a closed fixation loop for anchoring a catheter in any blood vessel, and more particularly, in the heart.

According to one embodiment of the present invention, there is provided transvenous leads including a ventricular lead having a wound coil, insulation covering the wound coil, an electrode secured to an end of the wound coil, and a plurality of tines extending outwardly from the electrode; an atrial lead having wound coil in coaxial alignment over the ventricular lead, insulation covering the wound coil, a ring electrode secured to an end of the wound coil, and two tines extending outwardly from the ring electrode, and; a fixation loop having a wound coil, insulation covering the wound coil and extending beyond each end of the wound coil of the fixation loop and secured over the tines of the ring electrode whereby the ventricular lead slides within the atrial lead for spacing of the ventricular electrode in the ventricular cavity and the atrial ring electrode in the atrium of the heart. A two-pronged connector includes a silicone body which securely affixes the atrial lead to one of the connector sleeves while the ventricular lead slideable moves within the other connector sleeve and is secured thereto with an O-ring which forms a liquid seal between the silicone rubber and the insulation.

A significant aspect and feature of the present invention is a closed fixation loop secured to a pacing lead for positioning and securing of the lead.

Another significant aspect and feature of the present invention is an atrial-ventricular coaxial lead. The atrial-ventricular coaxial lead provides for dual chamber pacing with a passage of one single lead through the body.

The atrial ventricular coaxial lead positioning is simpler and less time consuming in positioning the lead in the heart. The positioning of the lead is less traumatic than anchoring of electrodes in the chambers of the heart.

BRIEF DESCRIPTION OF THE DRAWINGS

Other objects and many of the attendant advantages of this invention will be readily appreciated as the same become better understood by reference to the following detailed description when considered in connection with the accompanying drawings, in which like reference numerals designate like parts throughout the figures thereof and wherein:

FIG. 1 illustrates a plan view of transvenous leads with a closed fixation loop;

FIG. 2 illustrates an end view taken along line 2—2 of FIG. 1;

FIG. 3 illustrates an exploded view of the fixation loop at an atrial ring electrode partially cutaway;

FIG. 4 illustrates an electrical connector; and,

FIG. 5 illustrates a cross-sectional view taken along line 5—5 of FIG. 4.

DETAILED DESCRIPTION OF THE PREFERRED EMBODIMENTS

FIG. 1, which illustrates a plan view of transvenous leads with a closed fixation loop, shows transvenous leads 10 including a ventricular lead 12, an atrial lead 14, a closed fixation loop 16, and a connector 18. The ventricular lead 12 as also illustrated in FIGS. 2 and 3 includes a quadra-filar space wound coil 20 such as an MP35N alloy by way of example and for purposes of illustration only extending a longitudinal distance, a ventricular electrode 22 secured to one end of the wound coil 20 and a proximal tip 24 at the other end of the wound coil 20. A polyurethane insulation coating 26 extends the distance of the wound coil 20 between the electrode 22 and the proximal tip 24. A tine support body 28 including a plurality of outwardly extending tines 28a–28d by way of example and for purposes of illustration only axially secures over the electrode 22 and abuts against a shoulder not illustrated in the figure of the electrode. The other end of the ventricular lead 12 slides through one connector sleeve 18b of the connector 18 as later described in detail in FIGS. 4 and 5. A quadra-filar space wound coil 30 of similar structure and of a larger diameter than of the wound coil 20 coaxially extends over the polyurethane insulation coating 26 of ventricular lead 12 and is shorter in length with respect to the ventricular lead 12. An atrial ring electrode 32 connects to one end of the wound coil 30 and a connector pin 34 connects to the other end of the wound coil 30. A polyurethane insulation coating 36 extends the distance of the wound coil 30 between the ring electrode 32 and the connector pin 34. A tine support body 38 including tines 38a and 38b illustrated in FIG. 2 axially secures to the atrial ring electrode 32 and abuts against a shoulder 32a of the atrial ring electrode 32. The fixation loop 16 includes a longitudinal portion of quadra-filar space wound coil 40 similar in diameter to the wound coil 20 covered with polyurethane insulation coating 42 and having overlapping ends 44a and 44b of polyurethane insulation. Coating 42 axially secures over the tines 38a and 38b, and abuts up against and to the tine support body 38 as illustrated in FIG. 3 forming the closed fixation loop 16.

FIG. 2 illustrates an end view taken along line 2—2 of FIG. 1 where all numerals correspond to those elements previously delineated. The closed fixation loop 16 assumes a teardrop shape from the tines 38a and 38b of the tine support body 38.

FIG. 3 illustrates an exploded view of the closed fixation loop 16 secured to the tine support body 38 where all elements correspond to those elements previously delineated.

FIG. 4, which illustrates the electrical connector 18, shows the wound coil 30 of the atrial lead 14 electrically affixed to a connector pin 34 through one sleeve 18a of the elongated "Y" connector 18. The end 46a of the sleeve 18a is configured to functionally engage with a pulse generator. Sealing rings 48a, 48b, and 48c by way of example and for purposes of illustration only provide a seal between the pulse generator and the one sleeve 18a. Adhesive can be injected between the sleeve 18a and the connector pin 34 further sealing the two members together. The wound coil 20 including the polyurethane insulation coating 26 of the ventrical lead 12 slides through the other sleeve 18b of the connector 18 for a finite distance beyond the end 46b of the sleeve 18b. The other end 46b is likewise configured as is the end 46a. Two sealing rings 50a and 50b are likewise provided. An O-ring groove 52 positions between the sealing ring 50b and the end 46b as also illustrated in FIG. 5 and accepts an O-ring 54 which forms a liquid seal 56 between the connector sleeve 18b and the polyurethane insulation coating 26 of the wound coil 20.

FIG. 5, which illustrates the cross sectional view taken along line 5—5 of FIG. 4, shows numerals corresponding to elements previously delineated.

PREFERRED MODE OF OPERATION

The transvenous leads 10 are inserted in through an appropriate vein in the human body towards the heart with the aid of a stylet and fluoroscope for precise positioning of the lead. Initially, the leads 12 and 14 are pushed together in a joint relationship down the vein until the outer lead 14 with the attached closed fixation loop 16 lodges in the atrium of the heat providing a sensory digital feedback signal to the medical personnel who subsequently pushes the inner lead 12 into the ventricle of the heart. Once proper positioning of the leads 10 has been achieved with the ventricle lead sliding within the other sleeve 18b of the connector 18, the O-ring 54, is positioned in the O-ring groove 52 thereby frictionally engaging the other sleeve 18b of the connector 18 to the polyurethane insulation coating 26 of the wound coil 20 of the ventricle lead 12. Subsequently the proximal tip 24 and the connector pin 34 are secured in the pulse generator for subsequent pacing of the individuals heart.

The diameter of the fixation loop 16 can be in the range of 20 mm to 105 mm by way of example and for purposes of illustration only. The French size of the atrial lead 14 and the fixation loop 16 can be in the range of 12 French by way of example and for purposes of illustration only.

Various modifications can be made to the fixation loop 16 for transvenous electrodes 10 of the present invention without departing from the apparent scope of the present invention. For instance, the length of the fixation loop 16 can be predetermined to fit any vein or cavity of the heart. The fixation loop 16 is not strictly limited to use with the leads 10 as disclosed but can be used with any surgical electrical lead.

Having thus described the present invention, there is claimed as new and desired to be secured by Letters Patent:

1. Body implantable pacing lead for insertion through a vein of the body into a cavity of a heart comprising: fixation loop including a longitudinal length of wound coil, a covering of insulation extending over and beyond the ends of said wound coil including an overlap at each end of said wound coil; and a transvenous lead including a wound coil, an electrode connected to a distal end of said coil and a covering of insulation over said wound coil of said lead and means joining each of said overlaps of said fixation loop to said insulation covering of said lead substantially adjacent to said electrode whereby said fixation loop positions said electrode within a cavity of the heart.

2. The lead of claim 1 wherein said fixation loop has a diameter of 20 mm to 105 mm.

3. Body implantable slideably adjustable pacing lead comprising:
   a. ventricular lead including a first space-wound coil, insulation covering said first space-wound coil, ring-tip electrode secured to one end of said first space-wound coil, and a plurality of tines extending outwardly from said insulation adjacent to said ring-tip electrode;
   b. atrial lead including a second space-wound coil in coaxial relation over said first space-wound coil, insulation covering said second space-wound coil, a ring electrode secured to said one end of said space-wound coil and two tines extending outwardly from said insulation adjacent to said ring electrode; and
   c. fixation loop including a space-wound coil, insulation covering said space-wound coil and extending beyond each end of said space-wound coil, and means securing overlapping ends of said extending insulation to said two tines whereby said ventricle lead coaxially slides within said atrial lead for spacing of said ventricle ring-tip electrode into a ventricular cavity and said atrial ring electrode in the atrial cavity.

4. The lead of claim 3 comprising:
   a. connector pin secured to the end of said atrial lead;
   b. proximal tip secured to the end of said ventricle lead, and;
   c. connector including two elongated sleeves encompassing and secured to said connector pin, the other of said connector sleeve surrounding and permitting sliding movement of said ventricle lead there through and means to secure said sleeve to said ventricle lead.

5. The lead of claim 4 wherein said securing means comprises an O-ring groove in said other sleeve and an O-ring which fits into said O-ring groove whereby said O-ring forms a liquid seal between said connector sleeve and said ventricle lead.

6. Fixation loop for a transvenous pacing lead including at least two tines extending outwardly from a distal end of said transvenous lead for anchoring said lead in a body comprising:
   closed fixation loop including a space-wound coil, insulation covering said space-wound coil and extending slightly beyond each end of said space-wound coil, and means securing overlapped ends of said extending insulation to said two tines of said transvenous lead whereby said closed fixation loop anchors said transvenous lead in said body.

7. The fixation loop of claim 6 wherein the diameter of said fixation loop is 20 mm to 105 mm.

8. A body implantable lead comprising:
   a first conductor having a proximal end and a distal end;
   a sheath of an insulating material substantially inert to body fluid covering said first conductor from said proximal end to said distal end;
   a first electrode coupled to said first conductor distal of said proximal end;
   a fixation loop having a first end attached to said sheath and having a second end attached to said sheath whereby said first electrode is urged into contact with body tissue.

9. A body implantable lead according to claim 8 wherein said first conductor is a first wound coil of conducting wire.

10. A body implantable lead according to claim 9 wherein said fixation loop further comprises:
    a coil having a first end and a second end;
    a protective covering of material substantially inert to body fluid covering said coil from said first end to said second end;
    a first tine attached to said sheath and attached to said first end of said coil whereby said first end of said coil is attached to said sheath; and
    a second tine attached to said sheath and attached to said second end of said coil whereby said second end of said coil is attached to said sheath.

11. A body implantable lead according to claim 10 wherein said first tine and said second tine are attached to said sheath at an equal distance from said proximal end of said first conductor.

12. A body implantable lead according to claims 8, 9, 10 or 11 further comprising:
    a second conductor having a proximal end and a distal end located within said sheath and mutually insulated from said first conductor;
    a second electrode coupled to said first conductor distal of said proximal end.

13. A body implantable lead according to claim 12 wherein said second conductor is a second wound coil of conducting wire.

* * * * *